(12) United States Patent
Hall et al.

(10) Patent No.: US 8,015,873 B2
(45) Date of Patent: Sep. 13, 2011

(54) DETECTOR HOUSING

(76) Inventors: David L. Hall, Luther, MI (US); Peter Stouffer, Holly, MI (US); James E. Ludwig, Clarksville, OH (US)

( * ) Notice: Subject to any disclaimer, the term of this patent is extended or adjusted under 35 U.S.C. 154(b) by 499 days.

(21) Appl. No.: 12/109,860

(22) Filed: Apr. 25, 2008

(65) Prior Publication Data

US 2009/0266183 A1 Oct. 29, 2009

(51) Int. Cl.
*G01D 11/24* (2006.01)

(52) U.S. Cl. ......................................................... 73/431

(58) Field of Classification Search .................... 73/431
See application file for complete search history.

(56) References Cited

U.S. PATENT DOCUMENTS

| | | | |
|---|---|---|---|
| 4,758,827 A | 7/1988 | Powers | |
| 5,103,212 A | 4/1992 | Notarianni et al. | |
| 5,396,796 A * | 3/1995 | Kotani et al. | 73/431 |
| 5,661,226 A * | 8/1997 | Bowers et al. | 73/24.01 |
| 5,844,148 A | 12/1998 | Klein et al. | |
| 6,124,795 A | 9/2000 | Bernau et al. | |
| 6,480,109 B1 * | 11/2002 | Tice | 340/506 |
| 2006/0027353 A1 * | 2/2006 | Luthi et al. | 165/11.1 |
| 2007/0139184 A1 | 6/2007 | Butalla, III et al. | |
| 2007/0139209 A1 | 6/2007 | Butalla, III et al. | |

FOREIGN PATENT DOCUMENTS

| | | |
|---|---|---|
| EP | 1006500 | 6/2000 |
| GB | 2347541 | 9/2000 |
| GB | 2351170 | 12/2000 |
| WO | WO2009015178 | 1/2009 |

OTHER PUBLICATIONS

SL-2000 Series Duct Smoke Detectors; Air Products and Controls.
SM-501 Series Duct Smoke Detectors: Air Products and Controls.

* cited by examiner

*Primary Examiner* — Hezron Williams
*Assistant Examiner* — Nathaniel Kolb
(74) *Attorney, Agent, or Firm* — Gifford, Krass, Sprinkle, Anderson & Citkowski, P.C.

(57) ABSTRACT

A duct detector housing includes a housing cover and a housing body defining a midline between the center of a detector and a printed circuit board within said body. Gas inlet and outlets are off axis of the midline to allow water that collects in conventional housing to drain from the housing. A maintenance mode button associated with a duct detector housing cover that is secured to a housing body of the housing provides a preselected time period during which removal of the cover is independent of a cover removal alarm. A printed circuit board within the housing has dedicated terminal blocks providing grouped connections with each of the groups segregated from another. An improved duct detector terminal has a hole in the terminal adapted to receive a test meter probe therethrough to provide an electrical contact between the wire.

8 Claims, 15 Drawing Sheets

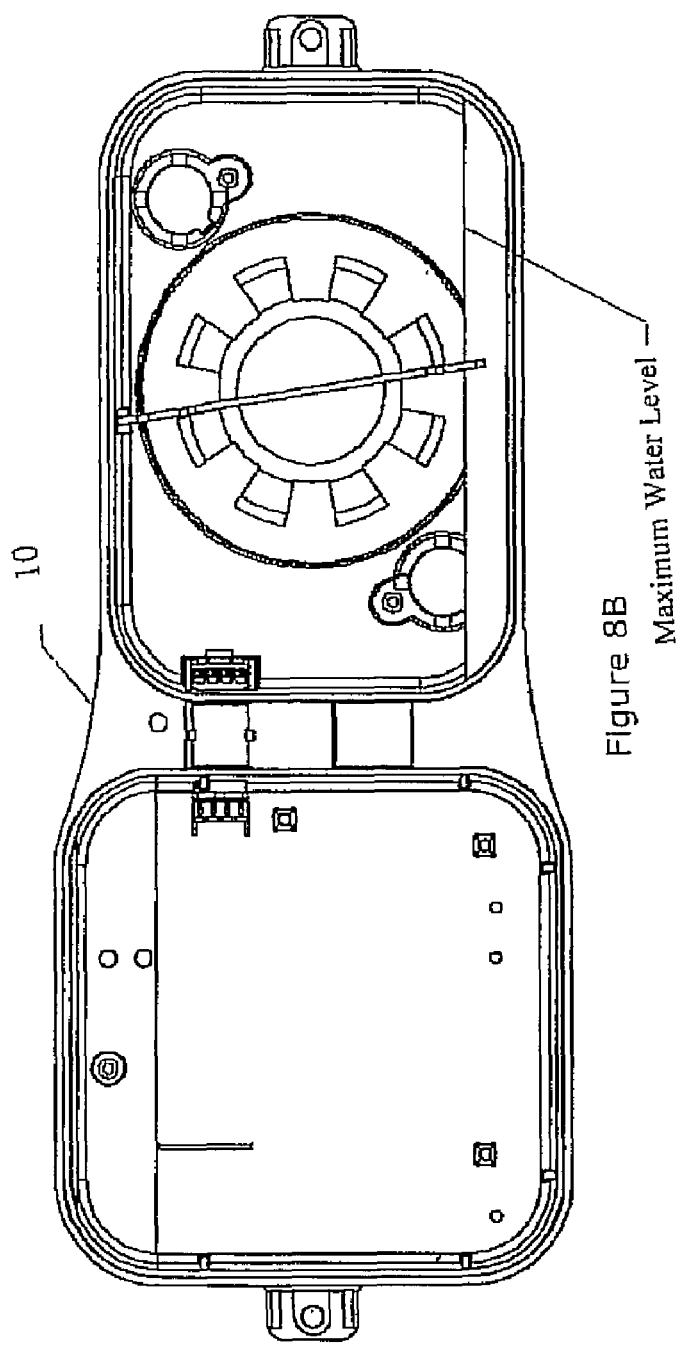

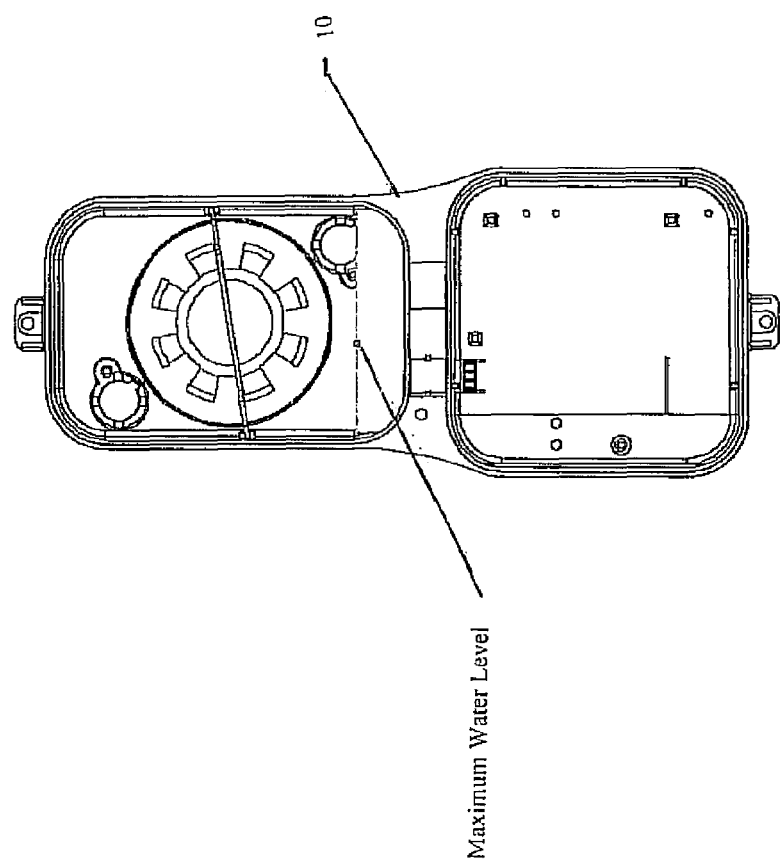

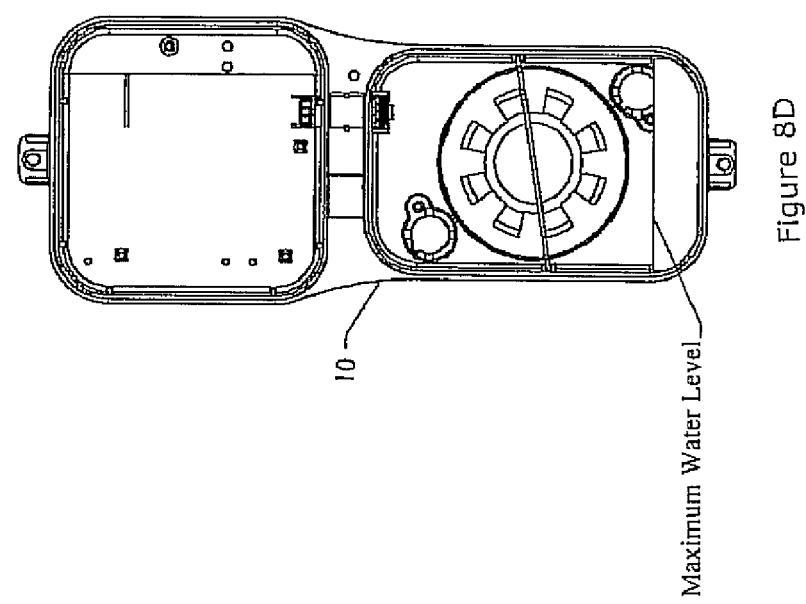

DETECTOR HOUSING

FIELD OF THE INVENTION

The present invention in general relates to an air handling detector housing, and in particular to a housing having components facilitating prolonged detector fail safe operation and efficient detector testing.

BACKGROUND OF THE INVENTION

Air handling duct systems are routinely fitted with air quality detectors such as smoke detectors or carbon monoxide detectors so as to detect an air quality problem and the resulting hazard before the gas is further distributed by the air handling system. Such detectors are routinely placed within a housing receiving inlet sample gas from an air handling system conduit and an outlet exhaust from which air handling system gas is returned to the same or different conduit of the air handling system so as to create a swirling flow pressure differential of air handling system gas around the detector within the housing. Such detectors are periodically tested to assure that a detector properly samples and signals an alarm in response to exposure to a target level of gas or activation of a test circuit.

A conventional air handling duct detector housing has a number of limitations that complicate testing and assured operation of a detector contained therein. A representative prior art air handling duct detector housing is provided in FIG. 1. A conventional housing has a body including midline inlet I and outlet O apertures along line M-M' for air to pass therethrough and a cover C that is often transparent that secures to the housing body by way of threaded fasteners F. The housing volume is proportioned and divided to accommodate a given detector D and related printed circuit boards P and electronics needed for coupling to a relay board, providing various normal, alarm, and trouble output signals and the like. The configuration of the air inlet and outlet apertures in communication with an air duct are routinely positioned midline within the housing as shown in FIG. 1. When moisture-laden air is conveyed through the air handling system, or alternatively the housing is at a lower temperature than the inlet air, condensation tends to collect within the housing. Under prolonged condensation conditions, water can accumulate in the housing to the midline of the housing resulting in active detector elements for electronic components being submerged in water resulting in emergency service to avoid component failure. Additionally, the seal line at the interface between the housing body and cover, while providing a generally waterproof seal, provides an inadequate barrier against vapor and the thermocycling associated with outdoor placement and as such a detector housing of FIG. 1 is limited to indoor placement. Still another limitation found in a conventional prior art housing is reliance on multiple threaded fasteners to provide a gradual tightening of the cover to the housing body. As a result a loose cover placement will not signal a warning and inhibit proper operation of a detector system. The simultaneous operation of a screwdriver to drive threaded fasteners while holding already removed fasteners, stabilizing the cover all while often balancing on a ladder also leads to inefficient servicing, unpredictable alarm operation and a falling hazard.

In view of the limitations found in a conventional prior art housing, there exists a need for an air handling system duct detector housing that is less vulnerable to detector failure through water egress and provides assured repeatability of sealing. There also exists a need for a detector housing that expedites detector testing and servicing and assures proper alarm operation.

SUMMARY OF THE INVENTION

A duct detector housing includes a housing cover and a housing body defining a midline between the center of a detector and a printed circuit board within the body. The housing body has a gas inlet and a gas outlet in fluid communication therewith. The gas inlet in fluid communication with a gas duct. The gas inlet and the gas outlet are off axis of the midline to allow water that collects in conventional housing to drain from the housing regardless of mounting orientation when the water reaches the level of either the inlet or outlet.

A process for testing a detector mounted within a duct housing sampling a forced air duct includes providing a maintenance mode button associated with a duct detector housing cover that is secured to a housing body of the housing and containing the detector therein. The maintenance mode button is activated to provide a preselected time period during which removal of tie cover is independent of a cover removal alarm. The cover is then removed, the internal detector tested and the cover replaced without a spurious alarm signal being recorded.

A duct detector housing includes housing cover and a housing body having a gas inlet and a gas outlet with the gas inlet in fluid communication with a gas duct and complementary to the cover to form an interface therebetween. The housing encompasses a detector and a printed circuit board within the housing body. The printed circuit board has dedicated terminal blocks providing grouped connections of at least fire alarm connections, detector interconnect connections remote access connections, HVAC connections and inlet power connections with each of the groups segregated from another.

An improved duct detector terminal including a wire entering a terminal and a clamping lever that engages the wire through a clamping mechanism has the improvement of a hole in the terminal adapted to receive a test meter probe therethrough to provide an electrical contact between the wire and a test meter without resort to disengaging the wire through operation of the lever.

BRIEF DESCRIPTION OF THE DRAWINGS

FIGS. 8A-8D are a schematic of water level management obtained through an inventive housing body of FIG. 6 regardless of mounting orientation;

DETAILED DESCRIPTION OF THE PREFERRED EMBODIMENTS

Figure 1:
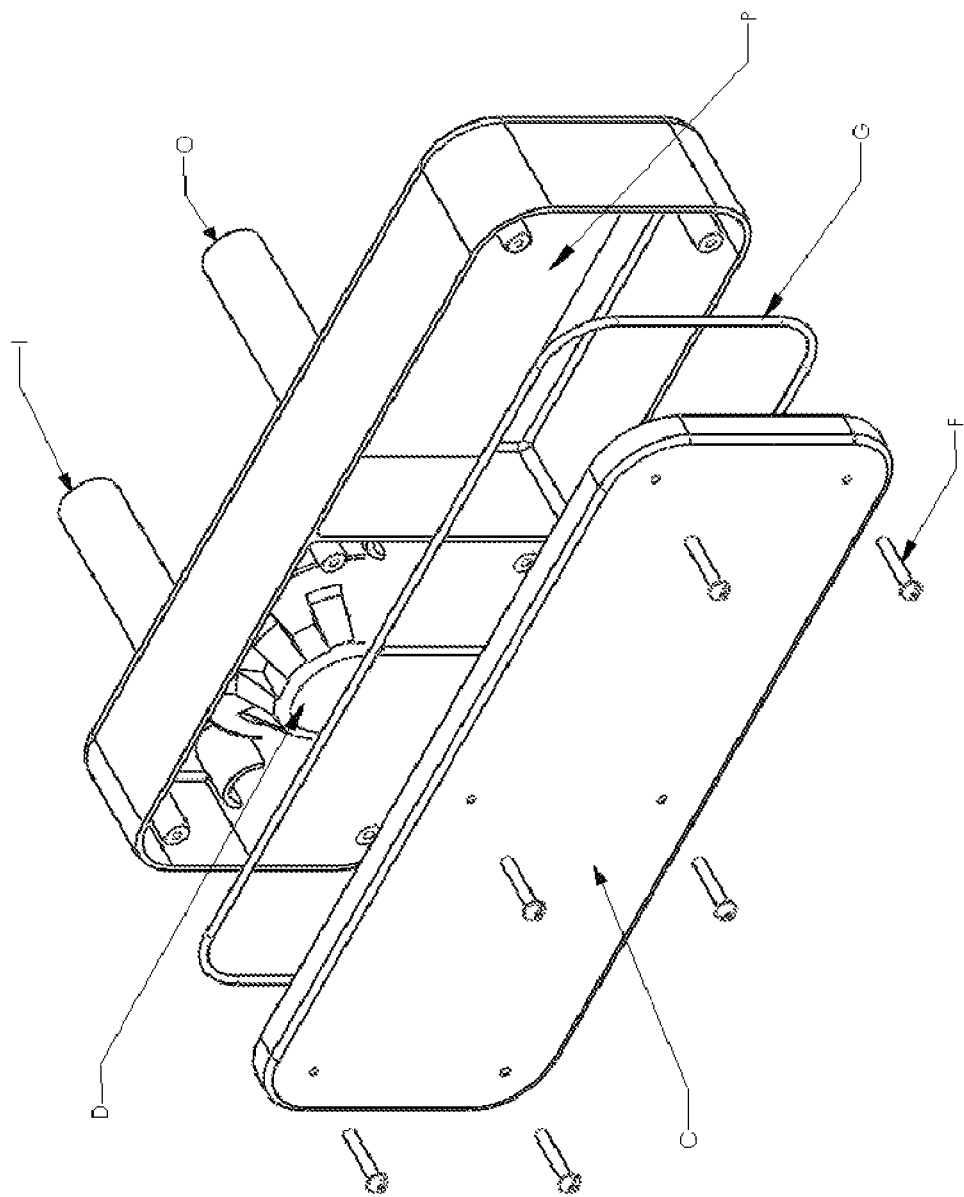
FIG. 1 is an exploded view of a prior art detector housing.
Figure 2:
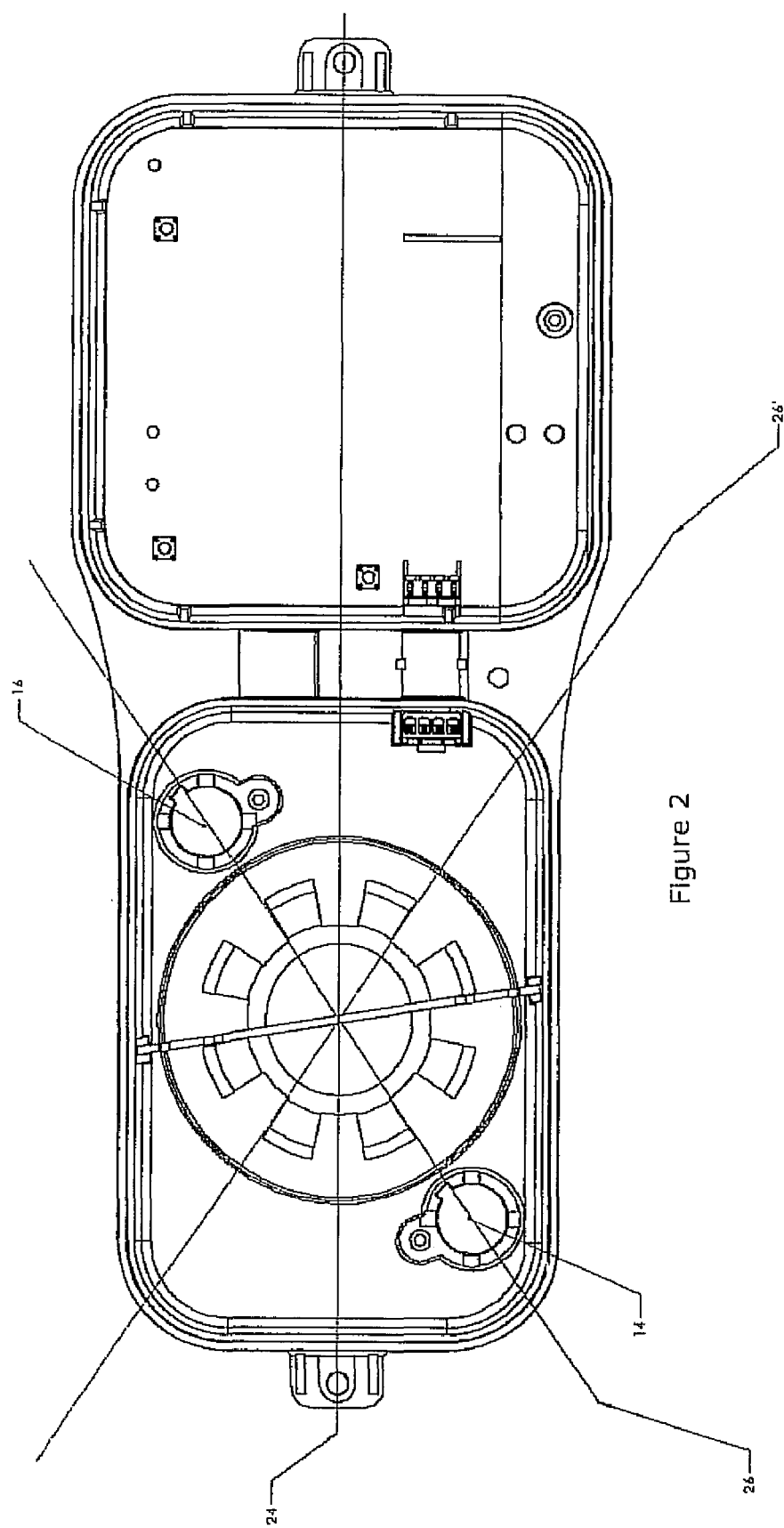
FIG. 2 is a plan view of an inventive detector housing.
Figure 3:
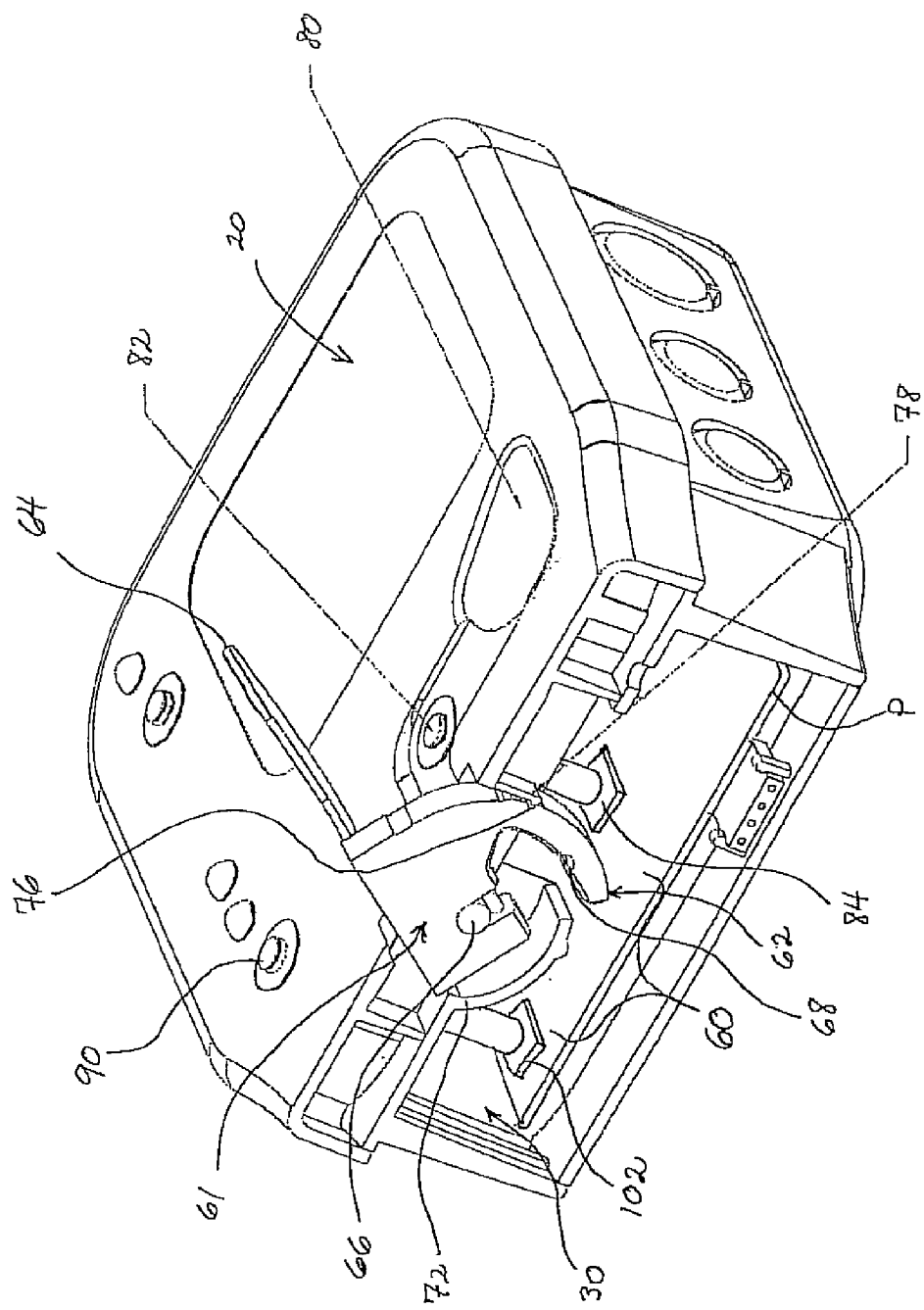
FIG. 3 is a partial cutaway view of the housing of FIG. 2 depicting a single latch binary securement depicted in an open position.

An inventive duct detector housing provides numerous improvements over the prior art housings as embodied in FIG. 1 with these improvements alone or in combination rendering more efficient the testing and maintenance of a detector enclosed within such a housing. The aspects of the present invention will be further detailed with respect to the following figures.

Referring now to FIGS. 2-9, an inventive housing is shown generally at 10. The housing 10 has a housing body 12 having an inlet 14 and an outlet 16. The inlet 14 is in fluid communication with an air flow through which air or any other flowing gas enters the housing 10 and into contact with a detector D energized and residing within a detector volume 18. The detector volume 18 is defined by the cavity formed within the housing body 12 upon mating with a complementary housing cover 20. The housing body 12 is formed from a variety of materials illustratively including steel, aluminum, thermoset resins, and thermoplastics. Preferably, the housing body 14 is formed of injection moldable thermoplastic such as Bayer Machrolon. The housing body 12 preferably includes a flange 22 adapted to pass a mechanical fastener therethrough so as to secure housing body 12 to a substrate. Typical substrates for mounting an inventive housing 10 are surfaces such as walls and air ducts. While it is conventional to position an inlet and outlet along a midline of the housing body per FIG. 1, preferably an inlet 14 and outlet 16 in a housing body 12 according to the present invention are positioned such that at least one of the inlet 14 or outlet 16 is positioned proximal to a bottom edge based on mounting orientation of an inventive housing 10 to a vertical substrate. As a result of at least one of the inlet 14 or outlet 16 being positioned proximal to the bottom edge of the housing 10 as mounted, condensation introduced into the housing detector volume 18 drains back through the bottom edge proximal inlet 14 or outlet 16 so as to preclude condensation water levels rising within the housing detector volume 18 to a level that impairs function or induces malfunction of the detector D housed within the volume 18. To facilitate joinder of inlet 14 and outlet 16 to tubing in fluid communication with an air duct, the portion of the inlet 14 and outlet 16 within the housing detector chamber 28 are preferably notched and have a securement as detailed in U.S. Pat. No. 7,204,822. More preferably, the inlet 14 and the outlet 16 are positioned diametrically relative to a central detector D so as to maintain conventional convection with the diametrically opposed inlet 14 and outlet 16 each being positioned at an angle of approximately 45 degrees removed from the midline 24 of the detector body 12. The two possible diametric lines positioning for inlet 14 and outlet 16 are denoted in FIG. 2 as 26 and 26'. Although the figures depict the inlet 14 and outlet 16 as being along line 26, it is appreciated that they are equally well positioned along line 26' to provide an equivalent diametric position with at least one of the inlet 14 or outlet 16 able to act as a drain of condensate regardless of whether an inventive housing 10 is mounted horizontally per FIGS. 8A and 8B, an inverted horizontal mounting per FIG. 8 or a vertical mounting of an inventive housing 10 per FIGS. 8C and 8D. The ability of inventive housing 10 having diametrically positioned inlet 14 and outlet 16 that are offset from midline 24 by an angle of between 30 and 60 degrees and preferably about 45 degrees to function as a condensate drain is depicted schematically in FIG. 2. While the housing body 12 is depicted with a rectilinear housing detector chamber 28, it is appreciated that a variety of other shapes are also amenable to the condensation drain aspects associated with placement of an inlet 14 or outlet 16 along a bottom edge relative to mounting position. These other shapes illustratively include circular, square, triangular and other regular and nonregular polygonal shapes.

The housing body 12 is optionally divided into a housing detector chamber 28 and a printed circuit board (PCB) chamber 30 that are physically isolated yet provide electrical communication therebetween. A printed circuit board (PCB) 32 is secured to the housing body 12 by way of anchor posts 34 extending into the PCB chamber 30. The advantage of physical isolation between housing detector chamber 28 and PCB chamber 30 is to isolate the electronics on PCB 32 from particulate and condensation associated with gas flow introduced by way of inlet 14. It is appreciated that a single chamber housing is readily provided and protection of PCB 32 provided by way of PCB 32 encapsulation. Preferably, the housing body 12 has one or more preformed apertures 36 or a thin-walled region 38 that upon dislodgement defines an aperture. An aperture 36 or a thin-walled region 38 is intended to provide a site for joinder of an electrical wire coupling 40.

Figure 7A:
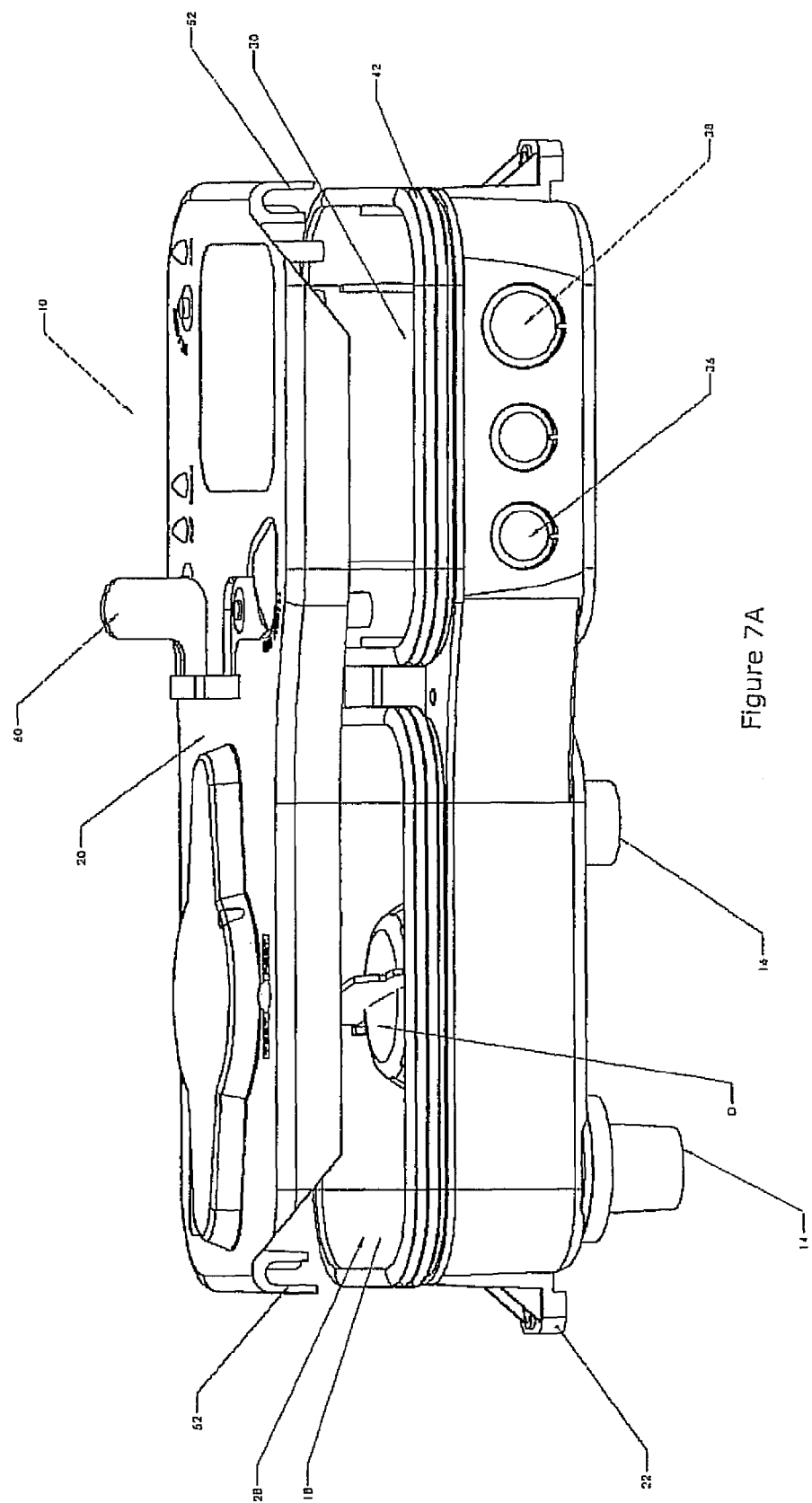
FIG. 7A is an exploded, partial cutaway, perspective view of the housing of FIG. 2 depicting an inventive cover seating system.
Figure 7B:
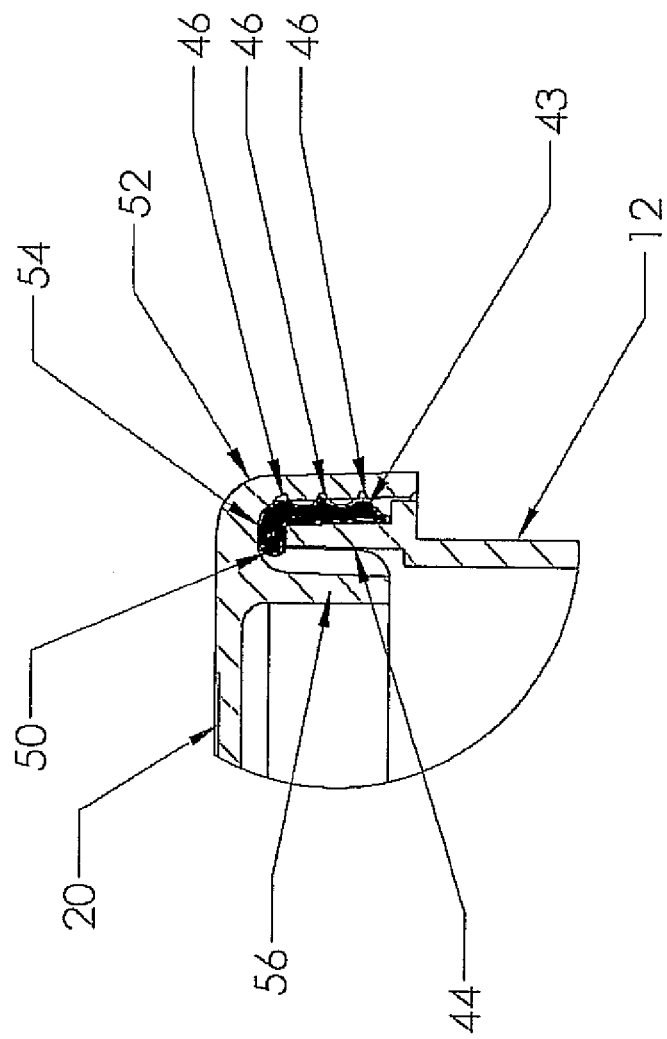
FIG. 7B is a magnified cross section of an inventive gasket closure in relation to a simultaneously contacting cover lip and housing extending wall surface of FIG. 7A.
Figure 8A:
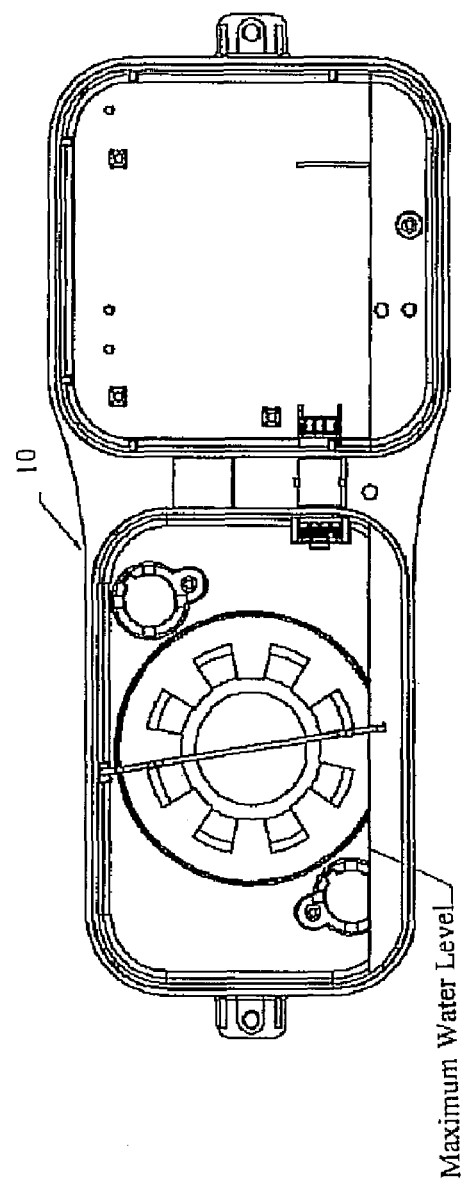
Figure 9:
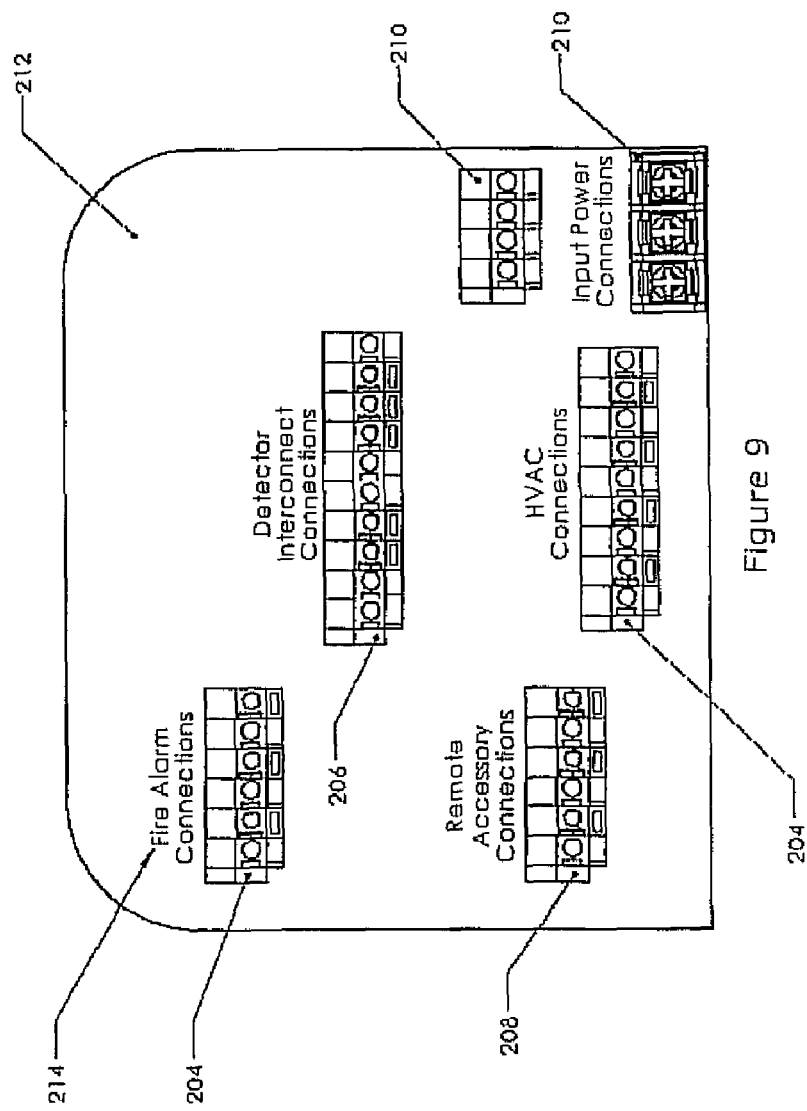
FIG. 9 is an inventive layout for a duct detector printed circuit board.

Intermediate between the cover 20 and the housing body 12 is a gasket. As depicted with respect to prior art FIG. 1, a circular, square or rectilinear cross section gasket G is press fit between a groove adapted to receive the gasket and a flat surface associated with the inner surface of a cover and housing body face. Unfortunately, such as gasket tends to be thin pinched by uneven pressure associated with fastener pressure urging the cover into contact with the gasket and the housing body thereby resulting in an unreliable seal. Additionally, single point of contact seals as well as fluid ingress by way of fastener holes precludes outdoor placement of such a prior art housing. In a preferred embodiment, an inventive gasket 42 having at least one lateral contact point 43 between a cover lip 52 encompassing an extending wall 44 of the housing body 12. The gasket 42 secures to an extending wall bounding one or both of the housing detector chamber 28 and the PCB chamber 30 in FIG. 7A. The extending wall 44 projects upward relative to housing body surface 46 as depicted in FIGS. 7A and 7B. The gasket 44 is adhesively secured to the extending wall 44 such that at least one protrusion from the gasket 42 extends outward relative to the extending wall 44 to form contact points 43 and preferably multiple contact points 43. More preferably, the gasket 42 has a top cap portion 48. Most preferably, the top cap portion 48 overhangs the extending wall 44 so as to overlie one of the housing detector chamber 28 or PCB chamber 30. The nature of the inventive gasket is best shown with regard to the magnified outset cross-sectional image provided in FIG. 7B. A cover 20 engaging an inventive gasket 42 has a cover lip 52 adapted to encompass the extending wall 44 with a degree of clearance such that the protrusions 46 are laterally compressed therebetween. The cover lip 52 intersects a covering surface 54 of the cover 20 and simultaneously compresses a top cap portion 48 of gasket 42, if portion 48 is present. Preferably, the cover 20 has an inner lip 56 adapted to engage an overhang portion 50 of the gasket 42, if present. In contrast to prior art gasket sealing schemes per prior art FIG. 1, an inventive sealing system involving a cover 20, housing body 12 and a gasket 42 preferably provides multiple contact points 43. With securement of a gasket 42 to an extending wall 44 with a conventional adhesive such as an acrylic adhesive, five separate gasket seal points are provided as depicted in FIG. 7B with three contacts associated with protrusions 46, one with top cap protrusion 48 and one with overhang portion 50. Such a gasket renders an inventive housing suitable for outdoor placement. An inventive gasket 42 requires a degree of compressibility difficult to achieve with a conventional solid neoprene gasket such as G of FIG. 1. Preferably, an inventive gasket is an expanded elastomer such as neoprene, latex, natural rubber, or other appropriate compounds either in singular or mixed compounds present as either an open-celled or closed-celled foam sponge. Preferably, the gasket 42 is a closed-cell foam so as to preclude water intercalation by way of gasket porosity.

Figure 4:
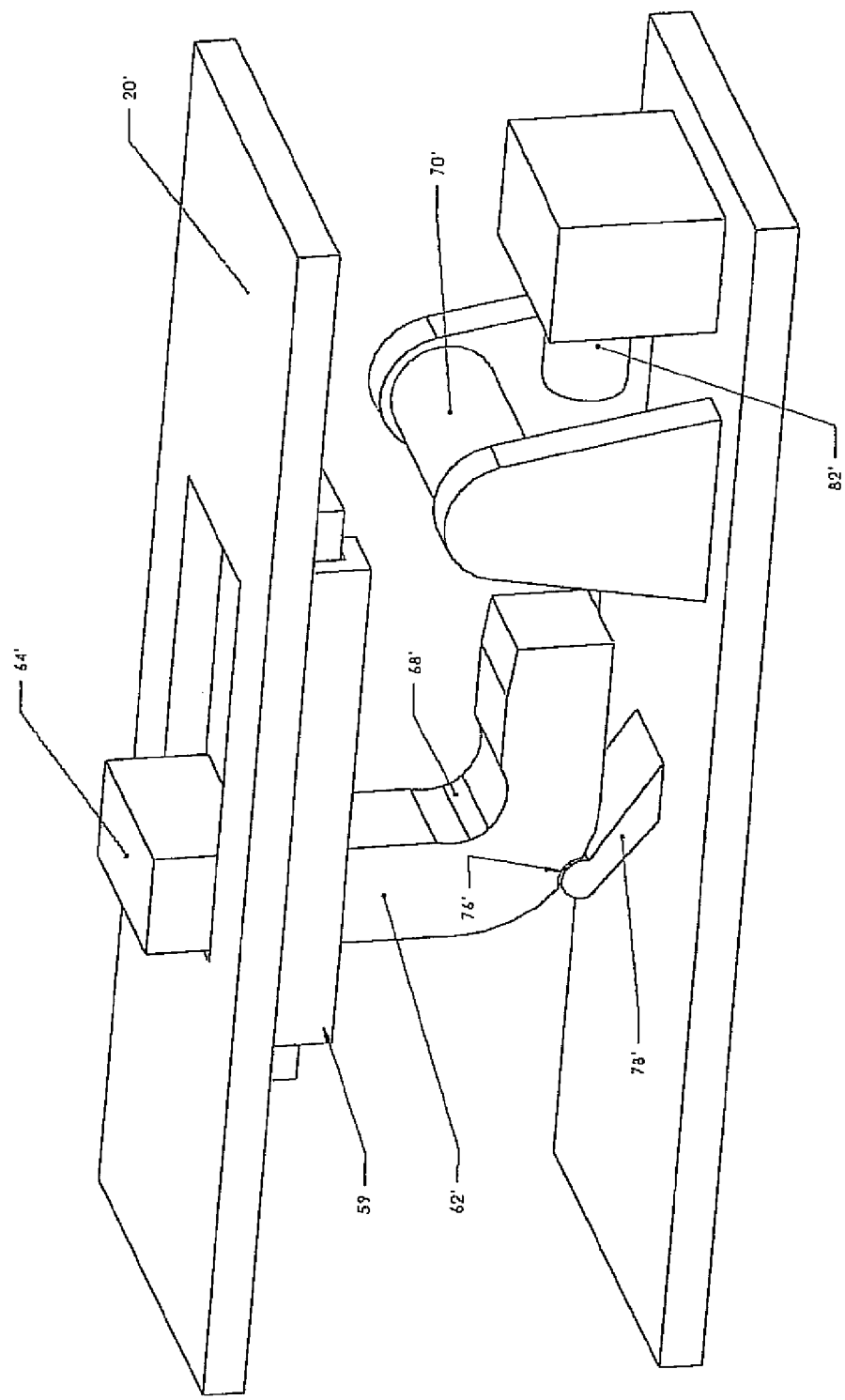
FIG. 4 is a perspective magnified view of a slide binary securement apparatus herein.
Figure 5:
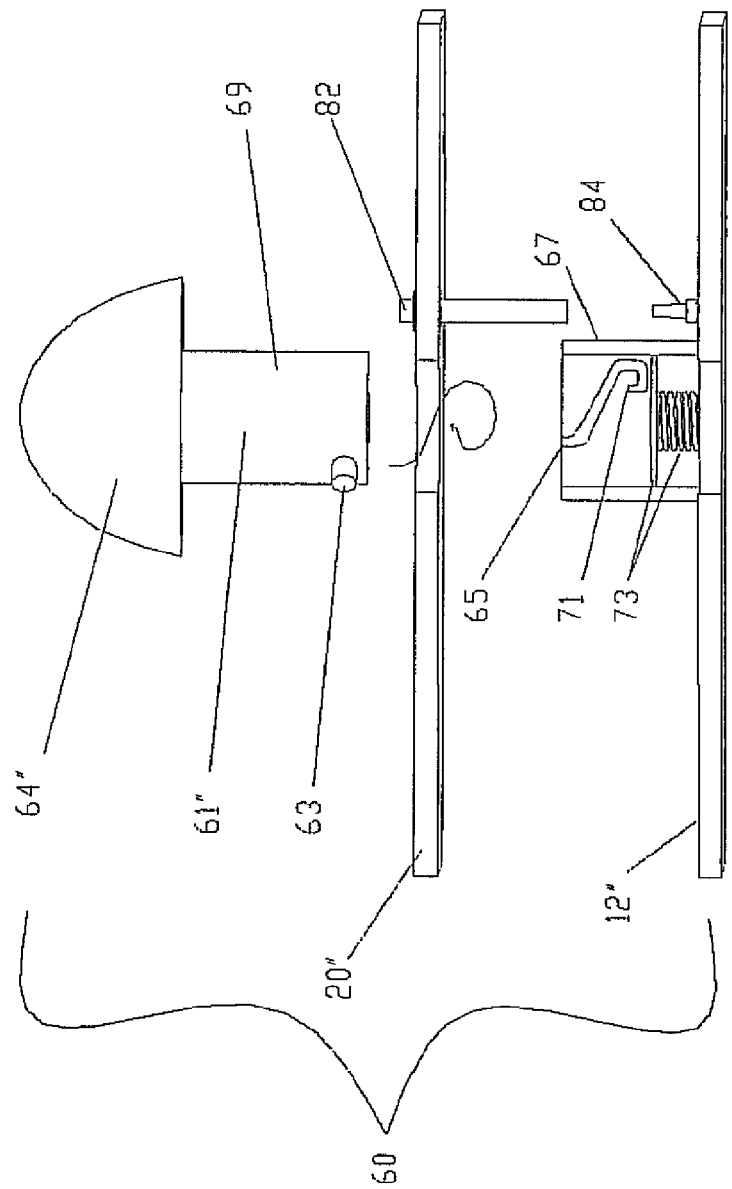
FIG. 5 is a cross-sectional magnified view of a bayonet binary securement operative herein.

An additional problem associated with conventional housings such as those of prior art FIG. 1, through resort to multiple mechanical fasteners to secure a cover to a housing body since integrity of the seal between cover and housing body is suspect owing to variables such as differential torque applied to fasteners, stripped fastener threads, and a missing fastener. Additionally, a technician standing on a ladder using one hand to position a cover by using the other hand to attempt to secure fasteners represents not only an installation and maintenance inefficiency but also a safety hazard. In order to overcome the limitations associated with multiple threaded fasteners used to secure a cover in place, an inventive housing 10 preferably resorts to a binary securement mechanism 60. The binary securement mechanism is distinguished over the prior art in having definitive "open" and "closed" positions that preclude the graded tightening of a threaded fattener. The binary mode securement mechanism 60 is depicted as a pivoting latch 61 in FIGS. 2, 3, 6 and 7; a sliding latch 61' as depicted in FIG. 4; and a bayonet latch 61" in FIG. 5. The binary mode securement mechanism 60 provides ease of cover securement while assuring seal integrity regardless of whether an inventive gasket 42 or a conventional gasket G is present at the interface between the cover 20 and the housing body 12. The latch 61-61" is typically formed of materials such as those from which the housing body 12 is formed and includes a hook engagement portion 62, 62' or a pin 63 and a handle portion 64-64". The latch 61 is pivotally secured to the cover 20 about a pivot pin portion 66 of the cover 20 of FIG. 3. The latch 61' is mounted to track 59 to slide laterally in the cover 20' of FIG. 4. Preferably, the hook engagement portion 62 or 62' has a first notch 68 or 68' in a complementary position relative to a catch 70 or 70'. The latch 61" of FIG. 5 press fits against cover 20" in response to a pin 63 engaging a groove 65 in a socket 67 adapted to receive cylindrical base 69 of the latch 61" with rotation of the handle portion 64". The groove 65 has a discontinuous closed portion 71 that assures a binary closed position. Preferably, a spring-loaded plate 73 ejects the base 69 to an "open" position when in a position other than the pin 63 engaging groove closed portion 71.

The common feature of binary mode securement mechanism 60 reproducible assurance that the latch 61-61" is either "open" or "closed." Preferably, the binary mode securement mechanism 60 is located intermediate between a housing detector chamber 28 and a PCB chamber 30 so as to assure a generally uniform circumferential pressure applied to a gasket 42 or G upon sealing of a cover 20-20" to a housing body 12-12". More preferably, a second notch 76 or 76' is provided that is complementary to a cover stay 78, 78' or 78' integral with the cover 20 or 20' such that the second notch 76 or 76' upon engagement of the cover stay 78 or 78" holds the binary mode securement mechanism 60 in an "open" position. It is appreciated that first notch 68 is readily placed on surface 72 while catch 70 is readily placed onto hook engagement portion 62 forming an inverted complementary pair of notch and catch. Likewise second notch 76 or 76' and cover stay 78 or 78' are readily inverted as to placement on hook engagement portion 62 or 62' and cover 20 or 20' to form an equivalent latch retention position. Still more preferably, an indent 80 is provided in the cover 20 adjacent to the handle portion 64 of the latch 61 when in a closed position. An indent 80 is provided to facilitate operation of the latch 61. Preferably, cover removal button 82 is provided to communicate to the cover removal switch 84 on a printed circuit board 32. The cover removal switch 84-84" sends an electrical signal based on whether the cover removal button 82-82" is depressed by the handle 64-64" or free of contact with the latch 61-61". Preferably, when a cover removal button 82 is present, the button is positioned in the cover 20-20" so as to be depressed when the handle portion 64-64" in a fully closed position. Alternatively, a cover removal button 82 is provided in an underlying relationship relative to mode binary securement mechanism surface 72 or 72' or plate 73 such that the hook engagement portion 62 or 62' or base 69 likewise depresses a cover removal button 82 when the mode binary securement mechanism 60 is in a closed position. It is appreciated that covers 20' and 20" as well as complementary housings 12' and 12" are identical to cover 20 and housing 12, respectively, with the exception of differences in securement mechanism 60 and description of other inventive attributes are equally operative therewith.

Optionally, a removable baffle 37 designed to insert within the housing detector chamber 28 serves to overlie the detector D and overlie at least one of inlet 14 or outlet 16 is provided to modify air circulation within the housing detector chamber 28 based on the performance characteristics of the detector D and the velocity of gas entering housing 10 by way of the inlet 14. An alarm test of detector D is optionally provided by inclusion of an elastomeric test port in the cover 20 as detailed in U.S. Pat. No. 6,741,181.

In a preferred embodiment, a cover 20 has exposed thereon a maintenance mode button 90, a test/reset button 92 and indicator lights indicative of pilot mode 94, trouble mode 96 and alarm mode 98. Preferably, the lights 94, 96, 98 are light emitting diodes (LEDs). An inventive housing 10 with the provision of buttons 80, 92, 94 and indicator lights 94, 96, 98 allows an installer, a service technician or an inspector of an inventive housing 10 to readily access sequence of operations for either indoor or outdoor units. In contrast to conventional detector test protocols initiated by removal of a cover, an inventive detector housing 10 eliminates dual trouble signals when trouble and alarm testing are performed on detectors associated with monitoring smoke alarm systems. As a result of the ability to initiate maintenance or test/reset detector associated electronics without cover removal, alarm cover removal switch 84 is not triggered in the process thereby simplifying system testing readout and test protocols.

Figure 6:
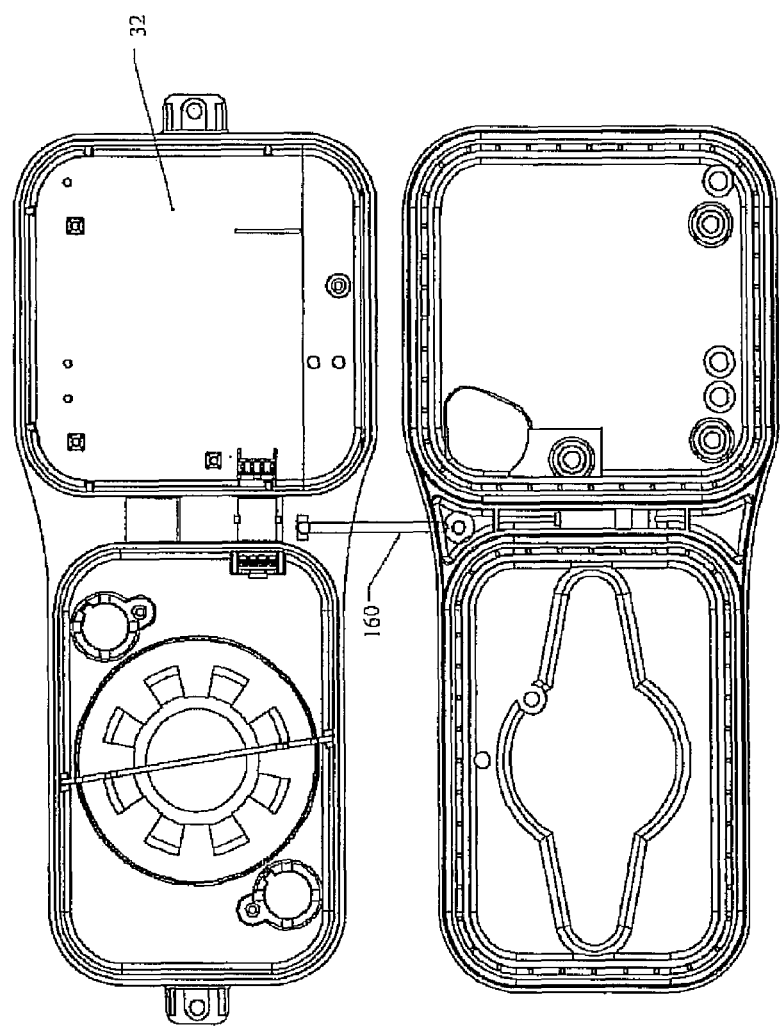
FIG. 6 is a plan view of the inventive housing of FIG. 2 with a housing cover hanging tethered to a housing body.

By way of example, operation of an inventive detector housing 10 in a maintenance mode is provided. The detector D and associated housing 10 in normal mode is indicated by operating power on, the cover 20 in place and pilot light 94 illuminated steady, preferably color coded as green; trouble indicator 96, preferably a yellow LED off; and alarm indicator 98 off, preferably in a red LED, as well as the trouble and test/reset buttons in normal inactive states 92 and 94. Depressing the maintenance button on the cover 20, housing body 12, or remote from the housing 10 activates a maintenance mode switch causing the pilot indicator light 94 to begin to flash which confirms maintenance mode initiation. A remote button is typically associated with a master control unit monitoring multiple detectors in multiple housings 10. Once maintenance mode button 92 has been pushed, the detector D goes into approximately a three minute timed test/maintenance mode where the front cover 20 can be removed for internal testing trouble and alarm functions of the detector D itself. Specific problems associated with the detector D which are tested for include proper placement of a detector head and an alarm caused by smoke testing of the detector head. During this three minute timed test, the position of the cover 20 does not affect the status of the detector housing 10. It is appreciated that this three minute timed test/maintenance mode is readily preselected to be a longer or shorter interval and is also well suited for troubleshooting minor wiring or electrical problems. While pilot light 94 is flashing, the trouble light 96 and alarm light 98 follow the actions as performed on the detector D itself. The alarm and trouble contacts on the printed circuit board P will also follow these actions as performed on the detector D for proper system integration testing. Upon proper replacement of the cover 20, the maintenance mode is automatically canceled but housing 10 reverts to normal operational status where failure of the cover 20 to be properly placed and the latch 60 closed to depress button 82 immediately causes a trouble condition. During the maintenance mode timing sequence optionally additional testing and maintenance time can be provided in three minute increments with a momentary repeated depression of the maintenance mode switch on the printed circuit board P that was previously engaged by depressing maintenance button 90. With depression of the maintenance mode switch, additional three minute increments of maintenance time are provided. In the event the maintenance mode switch is not activated to provide an additional three minute increment of operational time, the pilot indicator light 94 extinguishes and the trouble indicator 96 illuminates and the trouble contacts transfer immediately upon opening binary mode securement mechanism 60 and/or subsequent removal of the cover 20. A representative test sequence procedure includes: (1) Push maintenance mode button 90 momentarily and confirm mode activation by flashing pilot light optionally alternating with trouble indicator LED 96. (2) Unlatch latch 60 and remove cover 20. Preferably, a tether 100 as shown in FIG. 6 maintains the cover 20 in proximity to the housing body 12 after removal. (3) The head of the detector D is twisted out to verify proper unit and system trouble response. (4) The head of the detector D is twisted back into place to verify proper unit and system trouble restoral. (5) A smoke test for the detector D is used to provide proper unit and alarm response. (6) With the clearing of any residual smoke from the detector head and with momentary depression of the test/reset button 92, proper unit and system alarm restoral is confirmed. (7) The cover 20 is replaced and secured by pressing the latch handle portion 64 to a closed mode and in the process depressing a cover removal button 82, if present.

Preferably, while an inventive housing 10 is in maintenance mode, the flash rate of the pilot indicator light 94 begins flashing at a rate that increases as the timed maintenance mode period approaches within thirty seconds of preselected time sequence completion, or any other preselected window of time test completion. In the event that the maintenance mode button 90 is activated by mistake, maintenance mode button 92 is optionally depressed within a preselected amount of time within the initial depression such as for example ten seconds to cancel the maintenance mode request. An additional optional mode is that if the maintenance mode button 90 is activated and the binary mode securement mechanism 60 is not released within a preselected amount of time such as for example twenty seconds, the timed test/maintenance mode is terminated and the housing 10 is returned to normal mode as indicated by pilot indicator light 94 being continually green. It is appreciated that the lights 94, 96, 98 are mounted on an underlying printed circuit board P and visible through the cover 20 such that removal of cover 20 does not limit operational status information from installer or a service provider or an inspector during removal of the cover 20.

Figure 10A:
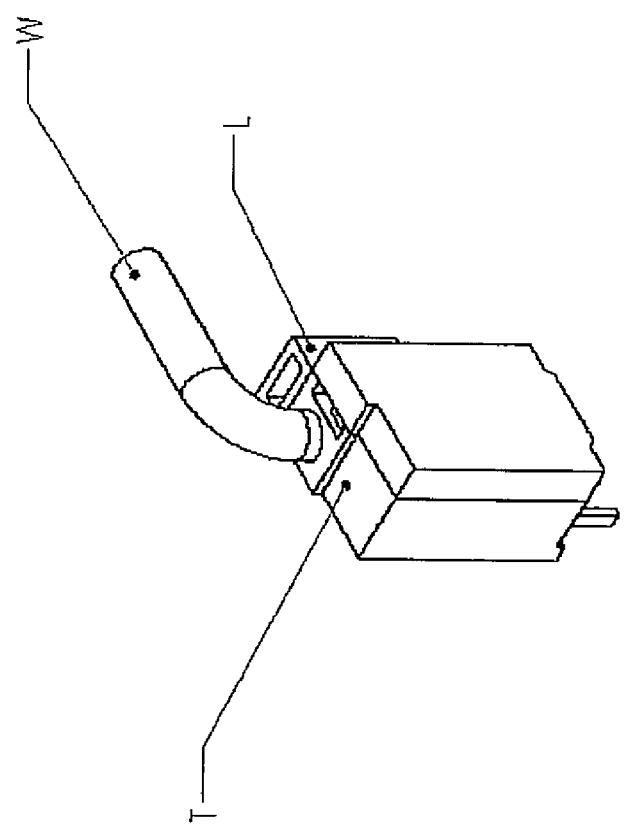
FIG. 10A is a perspective view of a conventional prior art node to a wiring terminal.
Figure 10B:
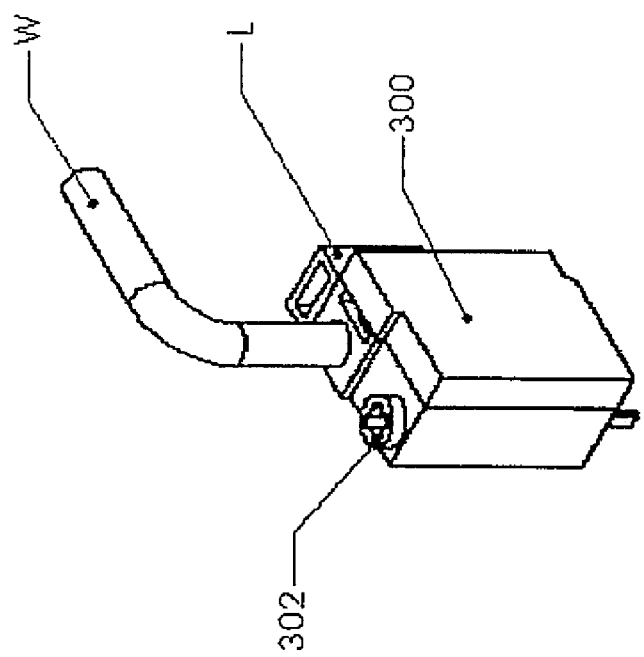
FIG. 10B is a perspective view of an inventive node to a wiring terminal including a test meter probe hole.

Referring now to FIG. 10, an inventive layout for a printed circuit board for inclusion in an inventive housing 10 is provided generally at 212. The printed circuit board 212 in contrast to a conventional PCB P segregates wire connection blocks based on individual specialists who may access an inventive housing 10. Specifically, terminal blocks are associated with fire alarm connections 202, HVAC connections 204, detector interconnect connectors 206, remote accessory connections 208 and input power connections 210 on PCB 212. With the provision of dedicated terminal blocks based on specialty, an individual accessing a PCB 212 for a specific purpose concentrates their energy on a collected set of connections related to their purpose instead of the same number of connections scattered across the surface of PCB 212. Preferably, indicia as to the nature of the terminal blocks 214 is provided on the board 212. More preferably, the dedicated terminal blocks 202-210 of PCB 212 are color coordinated.

Referring now to FIG. 11A, a conventional prior art terminal as used on PCB P is shown inclusive of a wire W entering the terminal T. A clamping lever L allows for selective securement or release of the wire W and the terminal T. The testing of terminal T and wire W currently requires the latch L to be operated to disengage the wire W.

FIG. 11B shows an improved inventive terminal 300 that represents an improvement over the prior art terminal depicted in FIG. 11A on the basis of providing a test meter probe hole 302 providing electrical continuity testing of the wire W without resort to operating the clamping lever L. Like numerals and letters are used to designate like components detailed above with respect to prior art FIG. 11A. With the provision of hole 302, the time of testing is reduced as well as the prospect of damaging by over stripping resulting in shock and short danger the contact between a wire W and a terminal T associated with unclamping and repeatedly clamping wire W with resort to lever L.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A duct detector housing comprising:
a housing cover; and
a housing body having a length and defining a midline parallel to said length, said midline extending through the center of a detector, and a printed circuit board within said body, said housing body having a gas inlet and a gas outlet, said gas inlet in fluid communication with a gas duct wherein the gas inlet and said gas outlet are off axis of the midline, on opposing sides of said midline, and on opposing sides of said detector.

2. The housing of claim 1 wherein said gas inlet and said gas outlet are diametrically opposed relative to the midline.

3. The housing of claim 1 wherein at least one of said gas inlet and said gas outlet are offset from the midline by an angle of between 30 and 60 degrees through the center of the detector.

4. The housing of claim 3 further comprising a binary mode securement mechanism for securing said cover to said housing body in either only an open or closed position.

5. The housing of claim 4 further comprising a gasket projecting outward from an extending wall of said housing body, forming at least one contact point when a cover lip of said cover encompasses the extending wall and said gasket.

6. The housing of claim 5 wherein said binary mode securement mechanism comprises a latch having a hook engagement portion and a handle portion, said latch pivotally or slidably secured to said cover and said housing body having a latching surface complementary to the hook engagement portion of said latch.

7. The housing of claim 6 further comprising a cover removal electrical switch button depressed by said latch being in a preselected position of either an open position or a closed position, said cover removal button being in electrical communication with a cover removal switch to provide a cover removal indicator signal.

8. The housing of claim 1 further comprising a maintenance mode button extending from said cover and engaging a maintenance mode switch on a printed circuit board located within said housing body allowing for removal of said cover for a preselected amount of time without triggering a cover removal alarm.

* * * * *